(12) United States Patent
Schuele et al.

(10) Patent No.: US 9,370,499 B2
(45) Date of Patent: *Jun. 21, 2016

(54) ANDROGEN RECEPTOR-DEPENDENT GENE EXPRESSION CONTROL

(71) Applicants: Roland Schuele, Weisweil (DE); Eric Metzger, Neuf-Brisach (FR)

(72) Inventors: Roland Schuele, Weisweil (DE); Eric Metzger, Neuf-Brisach (FR)

(73) Assignee: UNIVERSITAETSKLINIKUM FREIBURG, Freiburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/172,515

(22) Filed: Feb. 4, 2014

(65) Prior Publication Data

US 2014/0206770 A1 Jul. 24, 2014

Related U.S. Application Data

(63) Continuation of application No. 11/884,568, filed as application No. PCT/EP2006/001446 on Feb. 16, 2006, now Pat. No. 8,680,157.

(30) Foreign Application Priority Data

Feb. 18, 2005 (EP) .................................... 05003596

(51) Int. Cl.
| | | |
|---|---|---|
| A61K 31/138 | (2006.01) | |
| A61K 31/137 | (2006.01) | |
| A61K 31/7088 | (2006.01) | |
| C12Q 1/26 | (2006.01) | |
| C12Q 1/48 | (2006.01) | |
| G01N 33/74 | (2006.01) | |

(52) U.S. Cl.
CPC .............. *A61K 31/138* (2013.01); *A61K 31/137* (2013.01); *A61K 31/7088* (2013.01); *C12Q 1/26* (2013.01); *C12Q 1/48* (2013.01); *G01N 33/743* (2013.01); *G01N 2333/91011* (2013.01); *G01N 2500/04* (2013.01)

(58) Field of Classification Search
None
See application file for complete search history.

(56) References Cited

U.S. PATENT DOCUMENTS

| 6,432,991 B1 | 8/2002 | Thomas |
| 2005/0009835 A1 | 1/2005 | Thomas |

FOREIGN PATENT DOCUMENTS

| EP | 1329225 A2 | 7/2003 |
| WO | 0219964 A2 | 3/2002 |

OTHER PUBLICATIONS

Rose et al., J. Med. Chem. 2008, 51, 7053-7056.
Huang et al., PNAS, May 8, 2007, vol. 104 (19) pp. 8023-8028.
Stavropoulos et al., Expert Opinion in therapeutic targets, 2007, vol. 11 (6) pp. 809-820.
Quinn et al. (BJU International, 2002, vol. 9, 162-173.
Hau et al. (Mol. Endocrinol., Feb. 2006, 19 (2), 350-361.
Shi, Y. et al., Histone Demethylation Mediated by the Nuclear Amine Oxidase Homolog LSD1. Cell, vol. 119, 941-953 (2004).
Kubicek, S. et al., A Crack in Histone Lysine Methylation. Cell, vol. 119, 903-906 (2004).
Couzin, Jennifer, Molecular Biology. Long-Sought Enzyme Found, Revealing New Gene Switch on Histones, Science, vol. 306, 2171 (2004).
Strahl, B.D. & Allis, C.D., The language of covalent histone modifications. Nature, vol. 403, 41-45 (2000).
Chen D. et al., Regulation of Transcription by a Protein Methyltransferase, Science, vol. 284, 2174-2177 (1999).
Heinlein C.A. et al., Androgen Receptor (AR) Coregulators: an overview. Endocrine Reviews, vol. 23 (2) 175-200 (2002).
Glass, C.K. & Rosenfeld, M.G., The coregulator exchange in transcriptional function of nuclear receptors, Genes & Development, vol. 14, 121-141 (2000).
Shi, Y. et al., Coordinated histone modifications mediated by a CtBP co-prepressor complex Nature vol. 422, 735-738 (2003).
Hakimi, M.A. et al., A Candidate X-linked Mental Retardation Gene is a Component of a New Family of Histone Deacetylase-containing Complexes, J. Biol. Chem, vol. 278, 7234-7239 (2003).
Hakimi, M.A. et al., A core-BRAF35 complex containing histone deacetylase mediates repression of neuronal-specific genes, Proc. Natl Acad. Sci. USA vol. 99, 7420-7425 (2002).
Eimer, S. et al., Loss of spr-5 bypasses the requirement of the C.elegans presenilin sel-12 by depressing hop-1, The EMBO Journal, vol. 21, No. 21, 5787-5796 (2002).
Metzger, E. et al., A novel inducible transactivation domain in the androgen receptor: implications for PRK in prostate cancer, The EMBO Journal, vol. 22, No. 2, 270-280 (2003).
PubMed abstract of Schuele, R. et al., Functional antagonism between oncoprotein c-Jun and the glucocorticoid receptor, Cell, vol. 62(6), 1217-1226 (1990).
Verrijdt, G. et al., Functional Interplay between Two Response Elements with Distinct Binding Characteristics Dictates Androgen Specifically of the Mouse Sex-limited Protein Enhancer, J. Biol. Chem., vol. 277, 35191-35201 (2002).
Sun, Z., Pan, J. & Balk, S.P., Androgen receptor-associated protein complex binds upstream of the androgen-responsive elements in the promoters of human prostate-specific antigen and kallikrein 2 genes, Nucleic Acids Res., vol. 25, 3318-3325 (1997).
Brummelkamp, T.R., Bernards, R. & Agami, R., A System for Stable Expression of Short Interfering RNAs in Mammalian Cells, Science, vol. 296, 550-553 (2002).

(Continued)

*Primary Examiner* — Misook Yu
*Assistant Examiner* — Kauser Akhoon
(74) *Attorney, Agent, or Firm* — Abel Law Group, LLP

(57) ABSTRACT

Disclosed is the use of at least one amine oxidase inhibitor for modulating the activity of the lysine-specific demethylase (LSD1) in a mammal and to pharmaceutical compositions for controlling the androgen receptor-dependent gene expression, comprising an effective dose of at least one amine oxidase inhibitor suitable for modulating the activity of the lysine-specific demethylase (LSD1) in a mammal.

5 Claims, 5 Drawing Sheets

(56) References Cited

OTHER PUBLICATIONS

Mueller J.M. et al., FHL2, a novel tissue-specific coactivator of androgen receptor, The EMBO Journal, vol. 19, No. 3, 359-369 (2000).

Mueller, J.M. et al., The transcriptional coactivator FHL2 transmits Rho signals from the cell membrane into the nucleus, The EMBO Journal, vol. 21, No. 4, 736-748 (2002).

Shang, Y., Myers, M. & Brown, M., Formation of the Androgen Receptor Transcription Complex, Molecular Cell, vol. 9, 601-610 (2002).

Shatkina, L. et al., The Cochaperone Bag-1L Enhances Androgen Receptor Action via Interaction with the NH2-Terminal Region of the Receptor, Mol. Cell. Biol., vol. 23, 7189-7197 (2003).

Schneider, R. et al., Direct Binding of INHAT to H3 Tails Disrupted by Modifications, J. Biol. Chem., vol. 279, 23859-23862 (2004).

Wiznerowicz, M. & Trono D., Conditional Suppression of Cellular Genes: Lentivirus Vector-Mediated Drug-Inducible RNA Interference, J. Virol., vol. 77, 8957-8961 (2003).

a b g h

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgggttgggt caggttttgg tt                                              22

<210> SEQ ID NO 2
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcttcccctg tttctagttg agtg                                              24
```

ANDROGEN RECEPTOR-DEPENDENT GENE EXPRESSION CONTROL

CROSS-REFERENCE TO RELATED APPLICATIONS

The present application is a continuation of U.S. application Ser. No. 11/884,568, the entire disclosure of which is incorporated by reference herein, which is a U.S. National Stage of International Application No. PCT/EP2006/001446, filed Feb. 16, 2006, which claims priority of European Patent Application No. 05 003 596.3, filed Feb. 18, 2005.

SEQUENCE LISTING

The instant application contains a Sequence Listing which has been submitted electronically in ASCII format and is hereby incorporated by reference in its entirety. Said ASCII copy, created on Mar. 26, 2014, is named 6118-P50119_SL.txt and is 836 bytes in size.

BACKGROUND OF THE INVENTION

1. Field of the Invention

The present invention relates to the use of at least one amine oxidase inhibitor for modulating the activity of the lysine-specific demethylase (LSD1) in a mammal or for the manufacture of a medicament for modulating the activity of the lysine-specific demethylase (LSD1) in a mammal. The invention also relates to a pharmaceutical composition for controlling the androgen receptor-dependent gene expression, comprising an effective dose of at least one amine oxidase inhibitor suitable for modulating the activity of the lysine-specific demethylase (LSD1) in a mammal. The invention also relates to a method for controlling the androgen receptor-dependent gene expression in a mammal, said process comprising the step of administering to said mammal, on a suitable route, an effective dose of a pharmaceutical composition modulating an activity of the lysine-specific demethylase (LSD1) in a mammal Finally, the invention also relates to assay systems allowing to test LSD1 modulators for their ability to modulate, preferably inhibit, LSD1 function.

2. Discussion of Background Information

The androgen receptor (AR) is a member of the steroid hormone receptor family of transcription factors which regulate diverse biological functions including cell growth and differentiation, development, homeostasis and various organ functions in a mammal, particularly in a human. By binding suitable ligands like androgens to the ligand binding domain, functions of the AR are activated which are essential for the differentiation, development and maintenance of male or female reproductive organs and non-reproductive organs (as, for example, the prostate or the mammae).

Transcriptional regulation by nuclear receptors such as the androgen receptor (AR) involves interaction with multiple factors that act in both a sequential and combinatorial manner to reorganize chromatin[1]. Central to this dynamic reorganization is the modification of core histones. The N-terminal tails of histones are subject to various covalent modifications such as acetylation, phosphorylation, ubiquitination and methylation by specific chromatin-modifying enzymes[2]. Histone methylation at specific lysine residues is linked to both transcriptional repression and activation. When searching for new AR interacting proteins, Lysine specific demethylase 1 (LSD1)[3] was found to be one example of the chromatin-modifying enzymes.

LSD1 contains a centrally located swirm domain which functions as a putative protein-protein interaction motif, and also contains a C-terminal amine oxidase (AO) domain that harbours the demethylase activity[3] (FIG. 1b). Endogenous LSD1 and AR associate in vivo in androgen-sensitive tissues such as testis (FIG. 1a). To map the interaction domain between LSD1 and AR in vitro, GST pull-down analyses with labelled LSD1 and mutants thereof together with GST-AR fusion proteins were performed. As shown in FIG. 1b, full-length LSD1, as well as the swirm domain (LSD1 175-246) and the AO domain (LSD1 247-852) associate with either the N-terminus (NTD), the DNA binding domain (DBD), or the ligand-binding domain (LBD) of AR. In contrast, neither the N-terminus of LSD1 (LSD1 1-174) nor the GST control interact with AR.

It was now surprisingly found that the demethylating enzyme LSD1 is expressed ubiquitously in human and murine fetal and adult tissues (FIG. 2a and data not shown). Furthermore, it was also detected that LSD1 is found in the same cells (and in the same sub-cellular areas) where the AR is located (FIGS. 2c, d). In the course of the research resulting into the present invention, the above (and further) findings led to the conclusion that the demethylating enzyme LDS1 may exert a controlling influence on androgen-dependent gene expression. Furthermore, it was found that monoamine oxidase inhibitors as, for example pargyline, clorgyline or deprenyl (=selegiline) may be used to control demethylase activity and thereby regulate the AR. Thus, a specific modulation of LSD1 activity might by a promising therapeutic target in tissues where the AR plays a pivotal physiological role.

SUMMARY OF THE INVENTION

Hence, the invention relates to the use of at least one amine oxidase inhibitor for modulating the activity of the lysine-specific demethylase (LSD1) in a mammal.

Furthermore, the invention relates to the use of at least one amine oxidase inhibitor for the manufacture of a medicament for modulating the activity of the lysine-specific demethylase (LSD1) in a mammal.

Preferred embodiments of the use-related aspect of the invention are set forth below.

Furthermore, the invention relates to a pharmaceutical composition for controlling the AR-dependent gene expression, comprising an effective dose of at least one amine oxidase inhibitor suitable for modulating the activity of the lysine-specific demethylase (LSD1) in a mammal.

Preferred embodiments of the pharmaceutical composition of the invention are set forth below.

The invention also relates to a method for controlling the androgen receptor-dependent gene expression in a mammal, said process comprising the step of administering to said mammal, on a suitable route, an effective dose of a pharmaceutical composition modulating an activity of the lysine-specific demethylase (LSD1) in a mammal.

Preferred embodiments of the method of the invention are set forth below.

The invention also relates to assay systems allowing to test LSD1 modulators for their ability to modulate LSD1 function, wherein at least one chemical substance assumed to exert modulation of LSD1 function is subjected to one or more reaction(s) wherein said LSD1 is involved under conditions similar or identical to physiological conditions.

Preferred embodiments of the assay systems according to the invention are set forth below.

BRIEF DESCRIPTION OF THE DRAWINGS

The invention is further explained in the following description by referring to the Figures. However, the embodiments addressed in the Figures are considered to only exemplify the invention and should not be construed to restrict the invention. In the Figures.

DETAILED DESCRIPTION OF THE INVENTION

Figure 1:
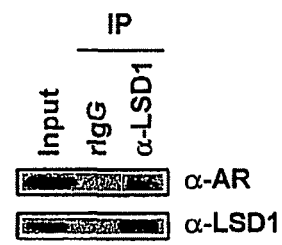
FIG. 1 shows the following: (a) LSD1 interacts with AR and LSD1 in vivo and in vitro. (b) AR co-immunoprecipitates with LSD1. Extracts from mouse testis were immunoprecipitated with an .alpha.-LSD1 antibody or control rabbit IgG. Ten percent of the extract used for immunoprecipation was loaded as input. Western blots were decorated with α-AR and α-LSD1 antibodies. a, GST pull-down assays were performed with labelled LSD1 mutants and the corresponding bacterially expressed GST-AR fusion proteins (150 mM KCl/ 0.15% NP40). GST proteins were used as control. (NTD; N-terminal domain, DBD; DNA-binding domain, LBD; ligand-binding domain).
Figure 1:
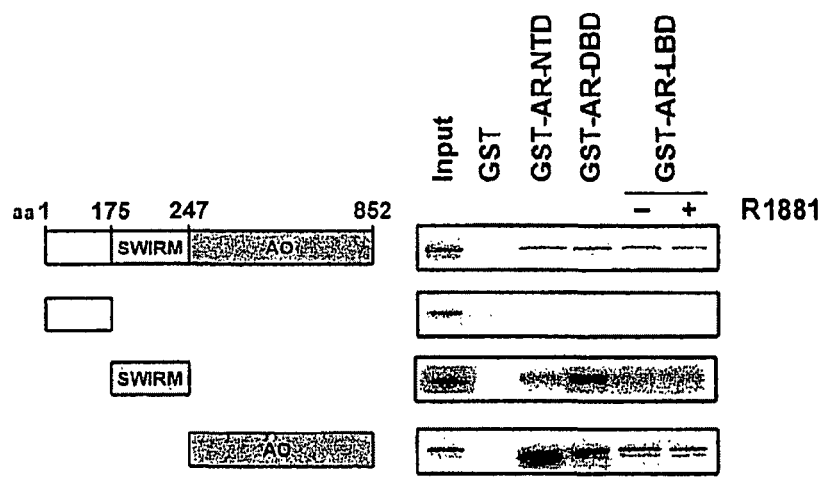

In a first aspect, the invention relates to the use of at least one amine oxidase inhibitor for modulating the activity of the lysine-specific demethylase (LSD1) in a mammal.

In a second aspect, the invention relates to the use of at least one amine oxidase inhibitor for the manufacture of a medicament for modulating the activity of the lysine-specific demethylase (LSD1) in a mammal.

In accordance with the invention, at least one amine oxidase inhibitor is used. There may be used one amine oxidase inhibitor or there may be used several amine oxidase inhibitors. In preferred embodiments of the invention, the use comprises one amine oxidase inhibitor. Any amine oxidase inhibitor may be employed in accordance with the present invention. However, in preferred embodiments, the at least one amine oxidase inhibitor or the one amine oxidase inhibitor is selected from the group of the monoamine oxidase inhibitors (MAOIs) comprising both monoamine oxidase A and monoamine oxydase B (MAO-A and MAO-B) inhibitors. These compounds can be nardil (phenelzine sulfate), phenelzin, parnate (tranylcypromine sulfate), tranylcypromine, isocarbazid, selegiline, deprenyl, chlorgyline, pargyline, furazolidon, marplan (isocarboxazid), 1-deprenyl (Eldepryl), moclobemide (Aurorex or Manerix), furazolidone, harmine, harmaline, tetrahydroharmine, nialamide, or any extract from plant, insect, fish, mammals that contains MAOIs. Even more preferably, the at least one amine oxidase inhibitor is selected from pargyline, clorgyline and deprenyl. Advantageously and, hence, most preferred, the amine oxidase inhibitor is pargyline.

According to the present invention, the at least one amine oxidase inhibitor is used, for example is used for the manufacture of a medicament, for modulating the activity of the lysine-specific demethylase, which is usually abbreviated as "LSD1". The term "modulating", as used in the present specification and claims, means a change either in the direction of improving the activity or in the direction of reducing the activity; in accordance with the invention, a blocking of the LDS1 activity is preferred.

In a preferred embodiment of the inventive uses, the activity of LSD1 modulated is the LSD1 demethylating activity. This means that the LSD1 exerts an influence as a catalyst in a chemical reaction where target methyl groups in a polymer molecule are removed, and thereby any influence on the molecule's activity is effected. To give just one example, an amine oxidase inhibitor used in accordance with a preferred embodiment of the invention may block demethylation of mono- and dimethyl H3-K9 during androgen-induced transcription. In a further preferred embodiment of the invention, when using at least one amine oxidase inhibitor, the demethylase activity of LSD1 controlled is the demethylating action of LSD1 on repressing histone marks on the histone H3 and/or the histone H4, preferably on repressing histone marks on the lysine residue 9 on the histone H3 (H3-K9), and/or the lysine residue 20 on the histone H4 (H4-K20), more preferably on the repressing histone marks on mono- and dimethyl H3-K9 and/or H4-K20, thereby increasing AR regulated gene expression.

In another preferred embodiment of the invention, the mammal in connection to which the amine oxidase inhibitors are used is a human. Even more preferred, when applying the invention to a human, the LSD1 demethylase activity is targeted to tissues where the AR plays a pivotal physiological role, preferably wherein the LSD1 demethylase activity is targeted to the brain, testis or prostate of a human, and/or any other tissue where both LSD1 and AR are co-expressed and co-localize.

In another aspect, the invention relates to a pharmaceutical composition for controlling the androgen receptor-dependent gene expression, comprising an effective dose of at least one amine oxidase inhibitor suitable for modulating the activity of the lysine-specific demethylase (LSD1) in a mammal.

In accordance with the invention, it is particularly preferred that the activity of LSD1 modulated by applying the at least one amine oxidase inhibitor is the demethylating activity of LSD1.

In a preferred pharmaceutical composition according to the invention, one amine oxidase inhibitor is used, although the use of more than one amine oxidase inhibitor is possible and may be advantageous. In even more preferred embodiments, the pharmaceutical compositions comprise at least one, particularly preferred exactly one amine oxidase inhibitor selected from the group of the monoamine oxidase inhibitors (MAOIs) comprising both monoamine oxidase A and monoamine oxydase B (MAO-A and MAO-B) inhibitors. These compounds can be nardil (phenelzine sulfate), phenelzin, parnate (tranylcypromine sulfate), tranylcypromine, isocarbazid, selegiline, deprenyl, chlorgyline, pargyline, furazolidon, marplan (isocarboxazid), 1-deprenyl (Eldepryl), moclobemide (Aurorex or Manerix), furazolidone, harmine, harmaline, tetrahydroharmine, nialamide, or any extract from plant, insect, fish, mammals that contains MAOIs, preferably wherein the amine oxidase inhibitors are selected from pargyline, clorgyline and deprenyl, more preferably wherein the amine oxidase inhibitor is pargyline.

It goes without saying that preferred pharmaceutical compositions according to the invention, in addition to the amine oxidase inhibitor, may contain further components which a skilled person may select in accordance with his ordinary skill. Those components may comprise solvents, carriers, excipients, auxiliary substances by which particular properties of the composition may be established and/or adjusted; such substances may exert an own effect or may contribute to contribute to effects exerted by other components. Examples of such additional substances can be selected by a person having ordinary skill in this technical field in accordance with the requirements, are will known and, hence, need no further detailed description here.

The invention, in another aspect, also relates to a method for controlling the androgen receptor-dependent gene expression in a mammal, said process comprising the step of administering to said mammal, on a suitable route, an effective dose of a pharmaceutical composition modulating an activity of the lysine-specific demethylase (LSD1) in a mammal.

In the method of the invention, it is preferred that the activity of LSD1 modulated is the LSD1 demethylating activity. In preferred embodiments of the method, the modulation is effected by means of at least one amine oxidase inhibitor. In a preferred method according to the invention, one amine oxidase inhibitor is used, although the use of more than one amine oxidase inhibitor is possible and may be advantageous. In even more preferred embodiments, the method comprise the application or administration of at least one, particularly preferred exactly one amine oxidase inhibitor selected from the group of the monoamine oxidase inhibitors (MAOIs) comprising both monoamine oxidase A and monoamine oxydase B (MAO-A and MAO-B) inhibitors. These compounds can be nardil (phenelzine sulfate), phenelzin, parnate (tranylcypromine sulfate), tranylcypromine, isocarbazid, selegiline, deprenyl, chlorgyline, pargyline, furazolidon, marplan (isocarboxazid), 1-deprenyl (Eldepryl), moclobemide (Aurorex or Manerix), furazolidone, harmine, harmaline, tetrahydroharmine, nialamide, or any extract from plant, insect, fish, mammals that contains MAOIs, preferably wherein the amine oxidase inhibitors are selected from pargyline, clorgyline and deprenyl, more preferably wherein the amine oxidase inhibitor is pargyline.

Particularly preferred embodiments of the method of the invention are characterized by that the demethylase activity of LSD1 controlled is the demethylating action of LSD1 on repressing histone marks on the histone H3 and/or the histone H4, preferably on repressing histone marks on the lysine residue 9 on the histone H3 (H3-K9), and/or the lysine residue 20 on the histone H4 (H4-K20), more preferably on the repressing histone marks on mono- and dimethyl H3-K9 and/or H4-K20, thereby increasing AR regulated gene expression.

The routes on which the administration of the effective dose of the pharmaceutical composition according to the invention to said mammal can be performed, can be any route of administration conceivable. The administration route may be selected by a skilled person in accordance with his ordinary skill and the requirements of the case. Just to mention few examples, the routes may be the oral, buccal, pulmonal, nasal, transdermal, intravenous, subcutaneous, intracutaneous, intramuscular, rectal, vaginal or intrathecal administration routes, optionally together with per se known carriers, adjuvants and additives. The oral, intraveneous, subcutaneous or intracutaneous administration routes are preferred.

With respect to the targets concerned, the LSD1 demethylase activity may be directed to any target in a mammalian body, particularly in a human body. Preferably, the LSD1 demethylase activity is targeted to tissues where the AR plays a pivotal physiological role, preferably wherein the LSD1 demethylase activity is targeted to the brain, testis or prostate of a mammal, preferably of a human.

The invention also relates to an assay system allowing to test LSD1 inhibitors for their ability to inhibit LSD1 function, wherein at least one chemical substance assumed to exert inhibition of LSD1 function is subjected to one or more reaction(s) wherein said LSD1 is involved under conditions similar or identical to physiological conditions.

The term "ability to modulate LDS1 function", as used in the present specification and claims, mean the ability of a chemical substance assumed or alleged to be a modulator of the enzyme Lysine specific demethylase (LSD1) to modulate the function of said enzyme. The modulation may either be an initiating and/or activating modulation or may be a decelerating or desactivating or inhibiting or even blocking modulation. In accordance with the assay system of the present invention, an inhibiting or blocking modulation is preferred.

As chemical substances, basically all chemical substances may be tested by the assay system of the present invention which substances are assumed or alleged to exert a modulating action on LSD1. The reaction(s) which is/are used in the assay system of the present invention may be one reaction or may be several reactions, e. g. a reaction sequence or reaction cascade where LSD1 is involved in one or several of the steps making up the reaction. In preferred embodiments of the assay systems of the present invention, the reaction(s) is/are (a) reaction(s) wherein LSD1 is also involved in its natural environment under natural conditions. In other words: The assay system of the present invention makes use of such biochemical reactions or physiological reactions wherein LSD1 is involved when exerting its natural modulating action, e. g. on the AR.

The term "physiological conditions" as used in the present specification and claims is understood to mean conditions which allow a mammal or, specifically, a human to exist and to be under acceptable living conditions without any undue burden concerning temperature, pressure, acidity/basicity, humidity/aqueous conditions of liquid systems, oxygen content of the gaseous environment etc. Such conditions are applied to the assay system of the present invention during the test phase. In accordance with preferred embodiments of the present invention, said physiological conditions are conditions established in conducting said assay system which are similar or identical to conditions present in one or more than one reaction(s) where LSD1 acts under physiological conditions.

A preferred embodiment of the present invention relates to an assay system, wherein the reaction the at least one chemical substance is subjected to, with the aim of modulating, preferably blocking said reaction, is the reaction of demethylation, by LSD1, on repressing histone marks on specific lysine residues of said histones. More preferably, the reaction is the reaction of demethylation, by LSD1, on repressing histone marks on the histone H3 or on the histone H4, more preferably is the reaction of demethylation, by LSD1, on repressing histone marks on the lysine residue 9 on the histone H3 (H3-K9) and/or the lysine residue 20 on the histone H4 (H4-K20), most preferably is the reaction of demethylation, by LSD1, on the repressing histone marks on mono- and dimethyl H3-K9 and/or H4-K20.

Another preferred embodiment of the present invention relates to an assay system, wherein the reaction the at least one chemical substance is subjected to, with the aim of modulating, preferably blocking said reaction, is the reaction of ligand-dependent LSD1-induced superaction of AR in 293- or CV-1-cells, thus modulating, preferably blocking the ligand-dependent AR activity.

A further preferred embodiment of the present invention relates to an assay system, wherein the reaction the at least one chemical substance is subjected to, with the aim of modulating, preferably blocking said reaction, is the reaction of androgen-dependent LNCaP- or MCF-7-cell proliferation, thus modulating, preferably blocking said androgen-dependent cell proliferation.

The invention is described in more detail below, without restricting it to those embodiments specifically addressed in the above description as well as in the subsequent description of preferred embodiments.

Figure 2:
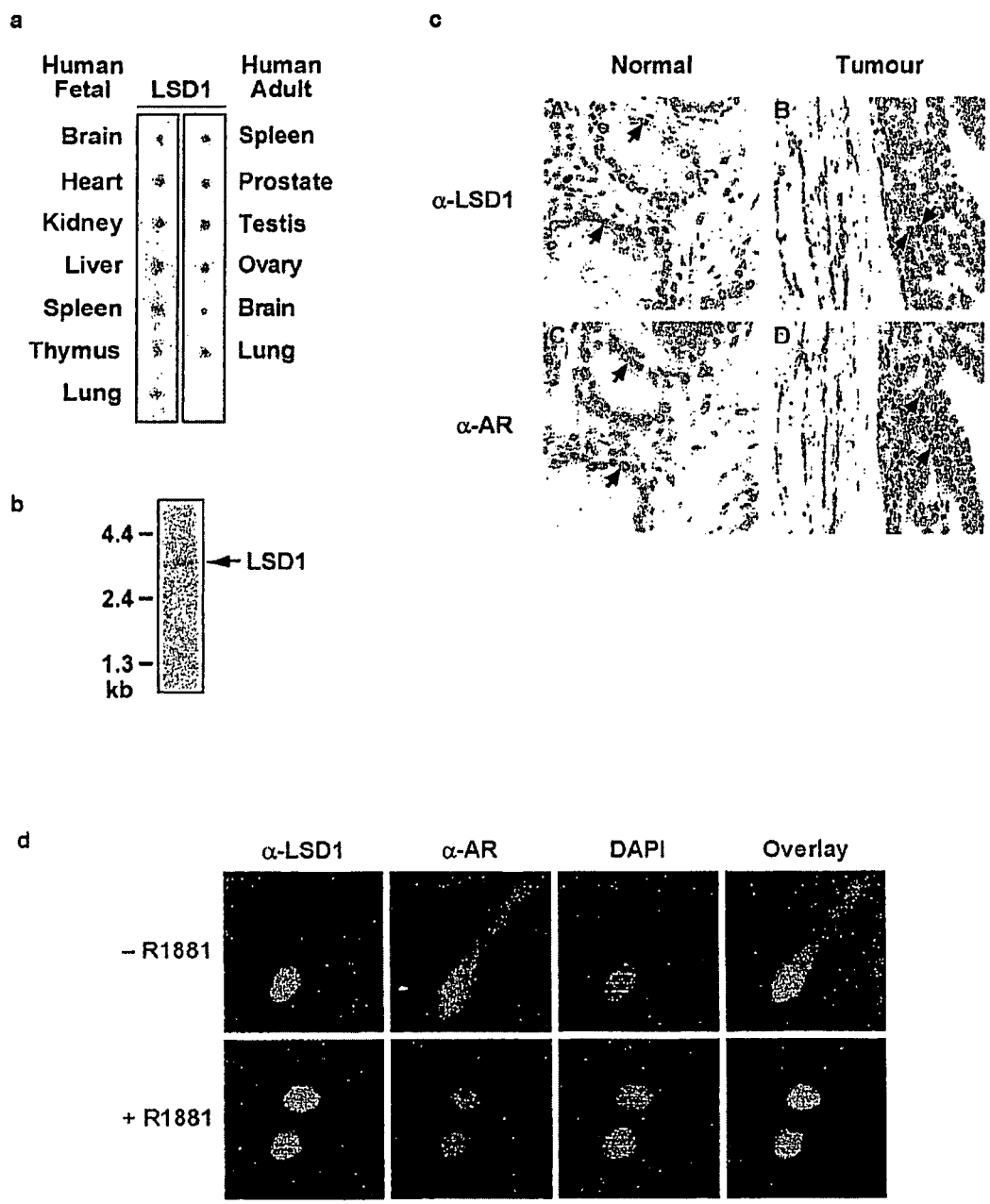
FIG. 2 shows LSD1 expression analyses. Expression of LSD1 mRNA in human tissues was examined by Northern blot analyses on a Human Multiple Tissue Expression Array (a) and a Northern blot of human testis (b). (c): Immunohistochemical staining of LSD1 and AR in human normal and tumour prostate. LSD1 (A, B) and AR (C, D) immunoreactivity is detected in the secretory epithelium of normal prostate (A, C, arrows) and tumour cells (B, D, arrows). All sections were taken from the same radical prostatectomy specimen. Magnification: X250. (d) Sub-cellular localization of endogenous LSD1 and AR in the human LNCaP prostate tumour cells. AR (red) co-localises with LSD1 (green) in the nucleus upon addition of the AR agonist+R1881.

To examine the expression pattern of LSD1, there were performed Northern blot analyses. LSD1 mRNA is ubiquitously expressed in human and murine fetal and adult tissues (FIG. 2a and data not shown) as a transcript of 3.3 kb (FIG. 2b). To investigate LSD1 localisation in prostate, there were used immunohistochemical analyses. As shown in FIG. 2c, LSD1 is detected in the epithelium of normal prostate and in tumour cells. Importantly, these cells also express AR (FIG. 2c) indicating that LSD1 and AR co-localise.

Next, the sub-cellular localisation of endogenous LSD1 and AR in human LNCaP prostate cancer cells was studied by immunofluorescence (FIG. 2d). LSD1 is present in the nucleus in the absence and presence of the AR agonist R1881. Addition of R1881 results in nuclear co-localisation of AR and LSD1. Taken together, the data show that LSD1 is a nuclear protein that co-localises with AR in androgen-sensitive tissues such as prostate.

Figure 3:
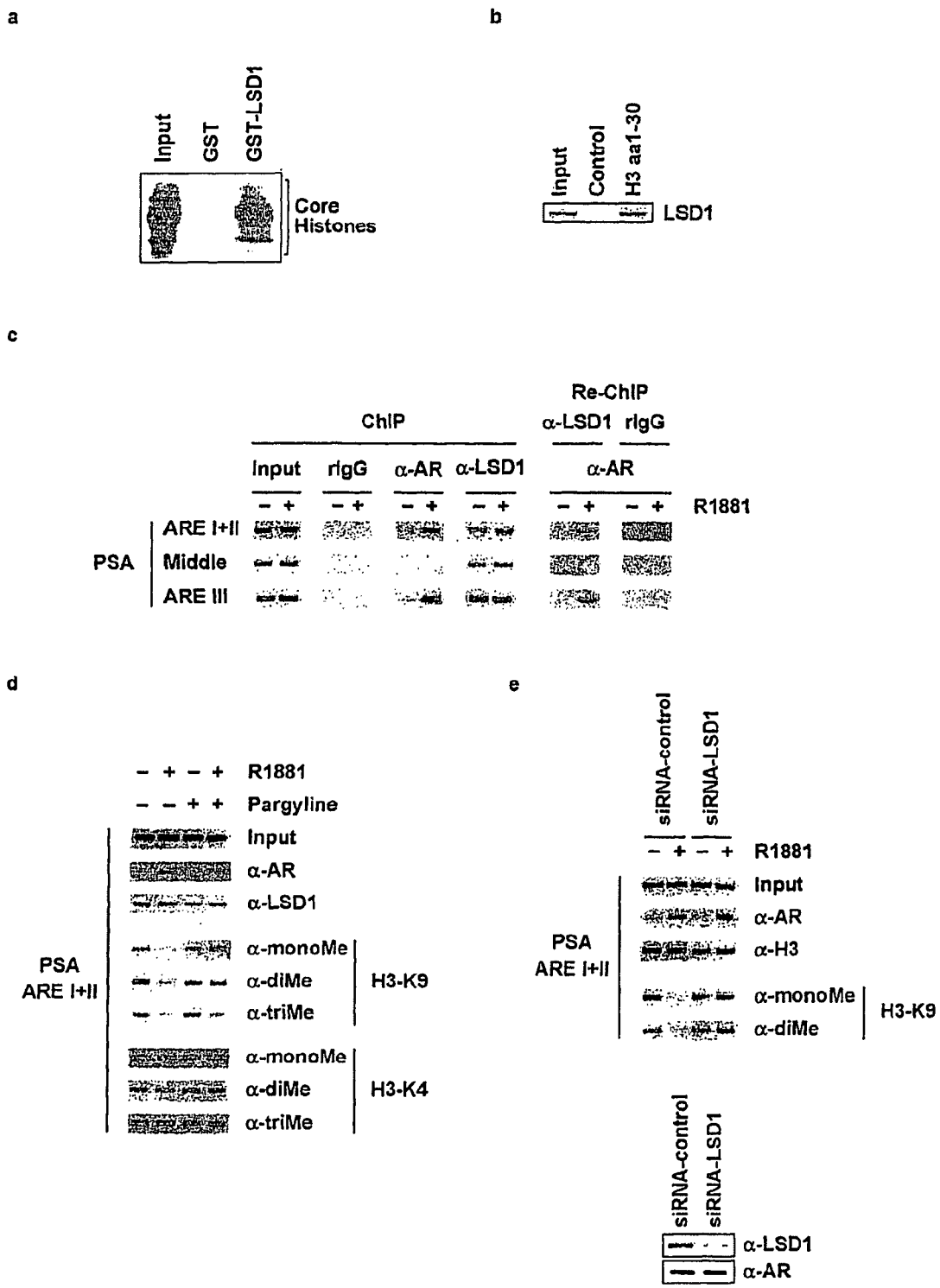
FIG. 3 shows how LSD1 interacts with chromatin: (a): Coomassie blue staining reveals interaction of bacterially expressed GST-LSD1 with core histones in vitro (600 mM KCl/0.3% NP40). (b): Labelled LSD1 interacts with the sepharose coupled N-terminal tail of histone H3. LNCaP cells were incubated with or without R1881 (c, d, e), treated with or without pargyline (d) or transfected with siRNA (e). ChIP or Re-ChIP were performed with the indicated antibodies. The precipitated chromatin was amplified by PCR using the primers flanking the promoter region (ARE I+II), the middle region (middle), or the enhancer region (ARE III) of the AR-regulated PSA gene. siRNA mediated knockdown of LSD1 is verified by Western blot analysis (e, lower panel) using α-AR and α-LSD1 antibodies.

Since LSD1 was found to associate with chromatin and demethylates H3-K4 in vitro[3], it was examined whether LSD1 directly interacts with core histones. Interaction analyses demonstrated physical association with core histones in vitro (FIG. 3a). Furthermore, the analyses show that LSD1 interacts with the N-terminal tail of histone H3 (FIG. 3b).

To determine whether LSD1 and AR associate with chromatin in vivo, LNCaP cells treated with R1881 were subjected to chromatin immunoprecipitation (ChIP). As shown in FIG. 3c, genomic DNA corresponding to the androgen response elements (ARE I+II and ARE III) located in the promoter and enhancer of the prostate specific antigen (PSA) gene, respectively was immunoprecipitated in a ligand-dependent manner with α-AR antibodies. Genomic DNA derived from a region between the enhancer and promoter was not enriched, thus demonstrating specificity (FIG. 3c). LSD1 associates with chromatin both in the presence or absence of ligand (FIG. 3c).

To demonstrate that LSD1 and AR form ligand-dependent complexes on chromatinized AREs, agonist-treated LNCaP cells were subjected to sequential chromatin immunoprecipitation (Re-ChIP), first with an α-AR antibody and next with either α-LSD1 or control α-rabbit IgG antibodies. Importantly, both ARE containing regions were enriched, demonstrating that LSD1 and AR form a ligand-dependent complex on chromatin (FIG. 3c).

Since PSA gene expression is induced by AR in an agonist-dependent manner the methylation levels of repressive histone marks were analysed, such as histone 3 at lysine 9 (H3-K9), histone 3 at lysine 27 (H3-K27), and histone 4 at lysine 20 (H4-K20). Androgen-induced transcription is accompanied by a robust decrease in mono-, di-, and trimethyl H3-K9 at the PSA promoter (FIG. 3d).

Since LSD1 is an AO that catalyses demethylation, a test was conducted whether monoamine oxidase inhibitors such as pargyline (N-methyl-N-2-propynyl-benzylamine), clorgyline (N-methyl-N-propargyl-3-(2,4-dichlorophenoxy-)propylamine) or deprenyl (=seregeline; (R)-(−)-N,2-dimethyl-N-2-propynylphenethylamine) might interfere with LSD1 function. Importantly, pargyline blocks demethylation of mono- and dimethyl H3-K9 during androgen-induced transcription, whereas methylation levels of trimethyl H3-K9 and the methylation status of H3-K27 and, H4-K20 remains unchanged (FIG. 3d and data not shown). Interestingly, methylation of histone H3 at lysine 4 (H3-K4) is not altered in vivo (data not shown).

To prove that the ligand-dependent demethylation of mono- and dimethyl H3-K9 is executed by LSD1, LNCaP cells were transfected with siRNAs directed against LSD1 or an unrelated control. This leads to efficient and specific down-regulation of endogenous LSD1, but does not affect the level of endogenous AR (FIG. 3e, lower panel). Importantly, LSD1 knockdown blocks ligand-dependent demethylation of mono- and dimethyl H3-K9 (FIG. 3e). The amount of total H3 is not influenced by LSD1 knockdown (FIG. 3e). Taken together, these data show the ligand-dependent association of LSD1 and AR on chromatinized AREs at the promoter of the PSA gene. This leads to the specific demethylation of the repressive histone marks mono- and dimethyl H3-K9.

Figure 4:
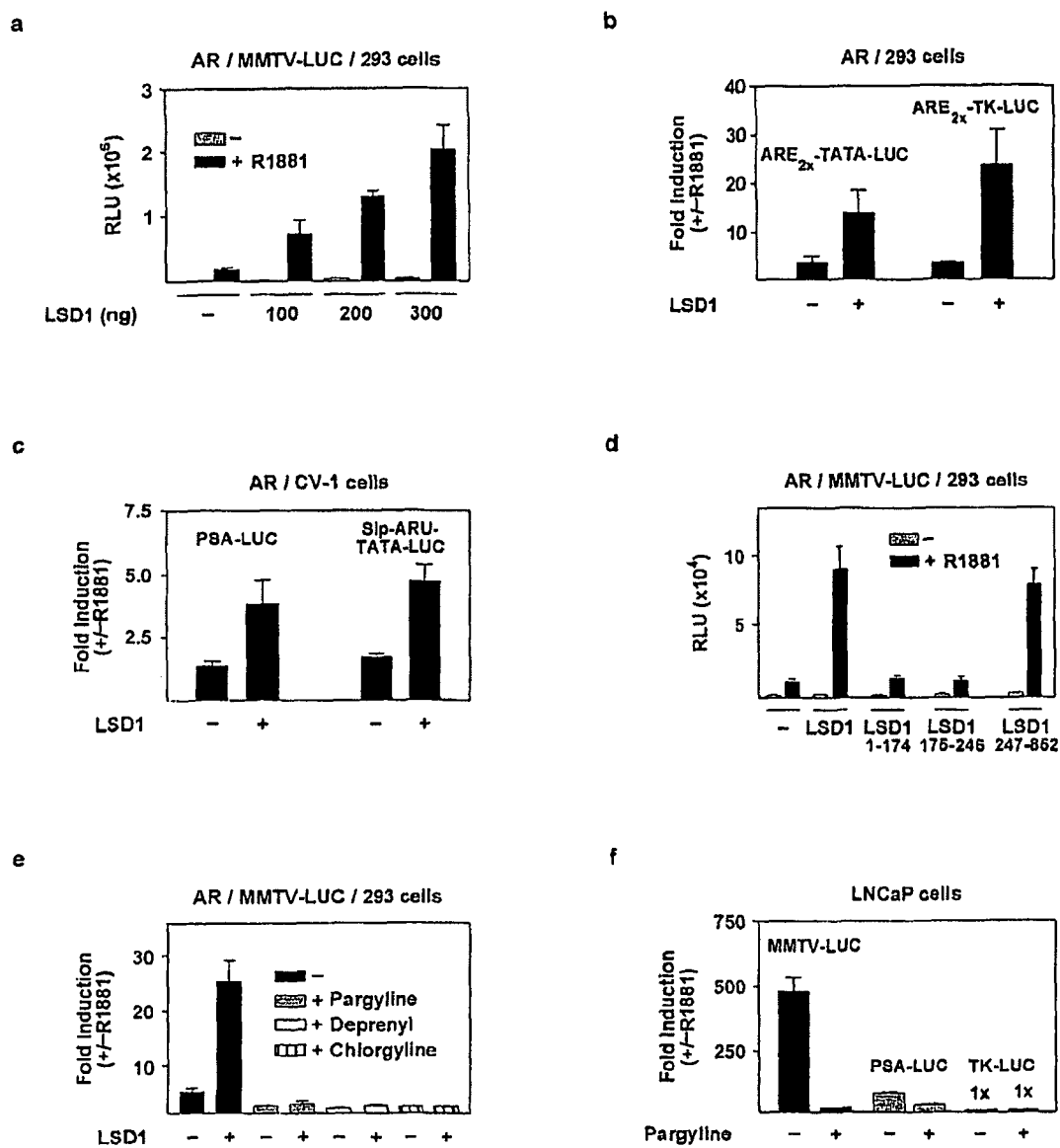
FIG. 4 shows how LSD1 controls AR-induced transcriptional activity and cell proliferation. 293 (a, b, d, e), CV-1 (c), and LNCaP (f, g) cells were transfected with the indicated AR-dependent reporters the in presence of AR expression plasmid (a-e). Cells were treated with or without R1881, pargyline, deprenyl, or chlorgyline. LSD1-induced ligand-dependent activation of AR (a, b, c) is mediated by the AO domain (LSD1 247-852, d) and blocked by monoamine oxidase inhibitors (e). In LNCaP cells, pargyline (f) and siRNA-mediated LSD1 knockdown block AR activity (g, left panel). LSD1 knockdown inhibits R1881-induced LNCaP cell proliferation (h, left panel). Knockdown of LSD1 is verified by immunofluorescence (g, right panel, arrows) and Western blot analysis (h, right panel) using α-AR and α-LSD1 antibodies. Bars represent mean+SD (≥5).
Figure 4:
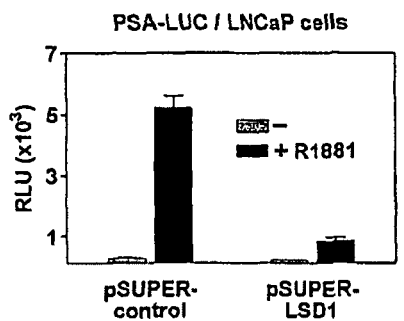
Figure 4:
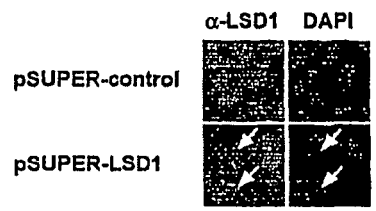
Figure 4:
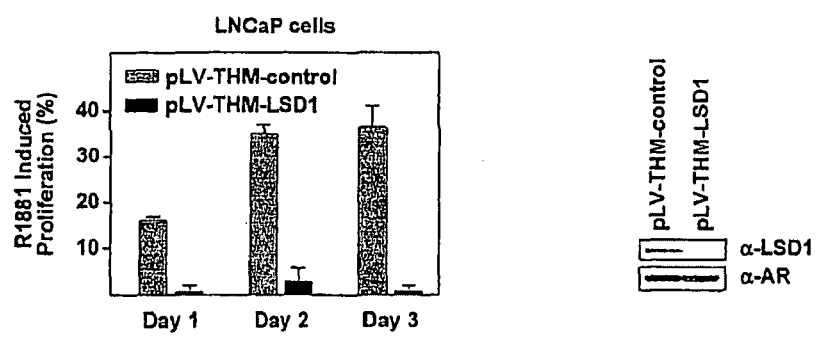

Next, there were performed transient transfection assays to test whether LSD1 modulates the transcriptional activity of AR. Co-expression of LSD1 and AR results in a strong ligand-dependent activation of an MMTV-luciferase reporter (FIG. 4a), which is not observed in the absence of either ligand or AR (data not shown). Stimulation of AR activity by LSD1 is potent in different cell lines, and both AR-responsive minimal, synthetic and complex promoters were activated by LSD1 in a ligand-dependent manner (FIG. 4b, c). Stimulation of AR activity is selective since LSD1 does not affect the transcriptional activity of the related steroid hormone receptors (data not shown).

Furthermore, it is demonstrated that the AO domain (LSD1 247-852) of LSD1 suffices to stimulate AR- and ligand-dependent reporter gene activity whereas the N-terminus (LSD1 1-175) and the swirm domain (LSD1 176-246) fail to do so (FIG. 4d). All LSD1 mutants are present in the nucleus and expressed at similar levels (data not shown).

To investigate if displacement of repressive histone marks by LSD1 results in increased AR regulated gene expression, monoamine oxidase inhibitors such as pargyline, clorgyline, and deprenyl were used in transient transfections. These inhibitors severely impair LSD1-induced activation of AR (FIG. 4e). Importantly, in LNCaP prostate tumour cells, which express endogenous AR, only androgen-dependent but not unrelated reporters such as TK-LUC are inhibited by pargyline, thus demonstrating specificity (FIG. 4f).

Next, endogenously expressed LSD1 was efficiently used in LNCaP cells by vector (pSUPER-LSD1) mediated RNAi (FIG. 4g, right panel). Paralleling LSD1 knockdown, a significant ligand-dependent decrease of PSA-LUC reporter gene expression was observed indicating impaired transcriptional activity of AR as a consequence of LSD1 knockdown (FIG. 4g, left panel). Since LSD1 governs AR transcriptional activity other androgen-controlled functions such as androgen-dependent cell growth might be regulated by LSD1.

To address this issue, LNCaP cells were infected with a lentivirus (pLV-THM-LSD1) expressing siRNA directed against LSD1. Infection with pLV-THM-LSD1 causes efficient and specific down-regulation of endogenous LSD1 but does not affect the level of endogenous AR (FIG. 4h, right panel). Importantly, when compared to cells transduced with the pLV-THM-control virus, androgen-induced proliferation of LNCaP cells is dramatically inhibited by pLV-THM-LSD1 mediated LSD1 knockdown (FIG. 4h, left panel). This data demonstrate the physiological importance of LSD1 in the control of androgen-induced gene regulation and cell proliferation.

In summary, the above data demonstrate that AR function is controlled by the demethylase LSD1. LSD1 and AR associate at chromatinized AREs of AR target genes a ligand-dependent manner, which results in concomitant demethylation of the repressive histone marks mono- and dimethyl H3-K9. LSD1 has been described as a component of co-repressor complexes[4-7] and a recent model proposes that LSD1 represses transcription of genes silenced by Co-REST due to demethylation of the activating histone marks on H3-K4[3]. However, when complexed with AR, LSD1 demethylates the repressing histone marks mono- and dimethyl H3-K9 and thereby promotes gene activation. Thus, depending on the specific interacting partners, LSD1 action might result in either gene silencing or activation. Of importance is our observation that inhibitors such as pargyline control the demethylase activity of LSD1 and thereby regulate AR. Thus, specific modulation of LSD1 activity might be a promising therapeutic target in tissues such as brain, testis, prostate where AR plays a pivotal physiological role.

Methods
Plasmids

The following plasmids were described previously: pSG5-AR, CMX-Flag, GST-AR-NTD, GST-AR-DBD, GST-AR-LBD, MMTV-LUC, and TK-LUC[8]; ARE$_{2x}$-TATA-LUC, ARE$_{2x}$-TK-LUC[9]; Slp-ARU-TATA-LUC[10]; PSA-LUC[11]; pLV-THM (www.tronolab.unige.ch/); pSUPER[12]. To construct CMX-Flag-LSD1, CMX-Flag-LSD1 1-174, CMX-Flag-LSD1 175-246, and CMX-Flag-LSD1 247-854 the corresponding fragments were amplified by PCR and inserted at the EcoRI/NheI site of CMX-Flag. pSUPER-control, pSUPER-LSD1 and pLV-THM-LSD1 were constructed according to (www.tronolab.unige.ch/) and as published[12]. Sequences can be obtained upon request.

Immunohistochemistry

Polyclonal rabbit α-LSD1 antibody was generated according to standard procedures. Stainings were performed using a protocol[13] for antigen retrieval and indirect immunoperoxidase. α-AR 441 (Santa Cruz) and α-LSD1 were used at a dilution of 1:75 and 1:500, rabbit IgG and mouse IgG (1:500; Dako) were used as secondary antibodies and immunoreactions were visualised with the ABC-complex diluted 1:50 in PBS (Vectastain, Vector).

Cell Culture and Transfections 293 and CV-1 cells were cultured and transfected as described[13]. LNCaP cells were cultured in phenol-red-free RPMI1640 supplemented with 10% double-stripped fetal calf serum (dsFCS) and transfected with Effectene (Qiagen). The following amounts per well were used: MMTV-LUC, ARE$_{2x}$-TATA-LUC, ARE$_{2x}$-TK-LUC, TK-LUC, PSA-LUC, Slp-ARU-TATA-LUC 500 ng each, 25 ng expression plasmids for AR; 500 ng expression plasmids for LSD1 1-174, LSD1 175-246, LSD1 247-852, pSUPER-control, and pSUPER-LSD1 100 to 500 ng expression plasmids for LSD1 were transfected per well. Chemicals were obtained as indicated: pargyline (Sigma); deprenyl and chlorgyline (ICN Biomedicals Inc.); R1881 (Schering AG, Berlin). Cells were treated with or without $10^{-10}$ M R1881, $3 \times 10^{-3}$ M pargyline, $1 \times 10^{-3}$ M deprenyl, or $1 \times 10^{-4}$ M chlorgyline for 18 hours as indicated. Luciferase activity was assayed as described[14]. All experiments were repeated at least five times in duplicate.

Chromatin Immunoprecipitation

ChIP experiments were performed essentially as described[15]. LNCaP cells were treated for 18 hours with or without pargyline and for 210 min with or without $10^{-8}$ M R1881 as indicated. LNCaP cells were transfected three days before harvesting for ChIP with or without siRNA (Qiagen) following the manufacture's instructions Immunoprecipitation was performed with specific antibodies (α-monoMeK9H3, α-diMeK9H3, α-triMeK9H3, α-monoMeK4H3, α-diMeK4H3, α-triMeK4H3, α-H3 (abcam), α-LSD1, and α-AR PG21 (Upstate Biotechnology) on GammaBind™-Sepharose 4B (GE-Healthcare). For PCR, 1-5 μl out of 50 μl DNA extract was used. For Re-ChIP assays, immunoprecipitations were sequentially washed with TSE I, TSE II, buffer III, and TE[15]. Complexes were eluted by incubation with 10 mM DTT at 37° C. for 30 min, diluted 50 times with dilution buffer[15] followed by a second immunoprecipitation with the indicated antibody. Primer sequences were as follows: middle; PSA (−2223/−1951) 5'-TGGGTTGGGT-CAGGTTTTGGTT-3' (SEQ ID NO: 1) and 5'-TCTTC-CCCTGTTTCTAGTTGAGTG-3' (SEQ ID NO: 2); PCR primers for ARE I+II (PSA (−459/−121)) and ARE III (PSA (−4288/−3922)) have been described previously[16].

Immunofluorescence

Cells were analysed essentially as described[14]. Primary antibody staining was performed with the indicated dilutions: α-AR 441 (1:500) and α-LSD1 (1:5000). Sub-cellular localisation was visualised using secondary Alexa Fluor 488- and 546-labelled antibodies (1:6000; Molecular Probes). Nuclei were stained with 1 μg ml$^{-1}$ DAPI (Roche).

Co-immunoprecipitation Assays and Western Blot Analyses

Experiments were performed essentially as described[8]. Immunoprecipitations from extracts of murine testis were performed with either α-LSD1 antibody or controlrabbit IgG. Western blots were decorated as indicated. Ten percent of testis extract was loaded as input.

In Vitro Pull-Down Assays

GST pull-down assays were performed with equal amounts of GST or GST fusion proteins as described[8] using buffer containing either 150 mM KCl, 0.15% NP40 (FIG. 1b) or 600 mM KCl, 0.3% NP40 (FIG. 3a). Pull-downs with sepharose coupled histone H3 tail were performed as described[17] in 20 mM Tris pH 8.5, 150 mM NaCl, 0.5% NP40. Ten percent of the in vitro translated proteins were loaded as input.

mRNA Analyses

Northern blot analyses were performed with a Human Multiple Tissue Expression Array and a Human Multiple Tissue Northern Blot (BD Biosciences Clontech) with an LSD1-specific probe spanning either by 1-741 or by 1-2556, labelled with StripEZ (Ambion), and hybridized as recommended.

Cell Proliferation Assay pLV-THM-control and pLV-THM-LSD1 were used to produce recombinant lenti-viruses to infect LNCaP cells as described[18]. The infected cells were cultured for 72 hours in medium supplemented with 10% dsFCS. $0.3 \times 10^4$ cells were plated in a 96-well plate with or without $10^{-7}$ M R1881. The cell proliferation Elisa BrDU Colorimetric Assay (Roche) was performed according to the manufacturer's instructions. The experiments were repeated three times in quadruplet.

Assay Systems

The invention describes the following assays to test LSD1 inhibitors in their ability to block LSD1 function and thereby AR.

1) The first assay to test inhibitors that block LSD1 and AR functions can be performed as shown in FIG. 3d. The inhibitor blocks the demethylation of LSD1 on repressing histone marks on the histone H3, preferably on repressing histone marks on the lysine residue 9 on the histone H3 (H3-K9), more preferably on the repressing histone marks on mono- and dimethyl H3-K9.
2) The second assay to test inhibitors that block LSD1 and AR functions can be performed as in shown in FIGS. 4e and 4f. An LSD1 inhibitor blocks the ligand-dependent LSD1 induced superaction of AR in 293 or CV-1 cells. An LSD1 inhibitor blocks the ligand-dependent AR activity.
3) The second assay to test inhibitors that block LSD1 and AR functions can be performed on cells that grow in an androgen-dependent manner such as LNCaP cells or MCF-7 cells. Such an inhibitor, similarly to siRNA mediated knockdown of LSD1 (FIG. 4h), blocks the androgen-induced cell proliferation.

LITERATURE

1. Glass, C. K. & Rosenfeld, M. G. The coregulator exchange in transcriptional function of nuclear receptors. *Genes Dev.* 14, 121-141 (2000).
2. Strahl, B. D. & Allis, C. D. The language of covalent histone modifications. *Nature* 403, 41-45 (2000).
3. Shi, Y. et al. Histone Demethylation Mediated by the Nuclear Amine Oxidase Homolog LSD1. *Cell* 119, 941-953 (2004).
4. Shi, Y. et al. Coordinated histone modifications mediated by a CtBP co-repressor complex. *Nature* 422, 735-738 (2003).
5. Hakimi, M. A. et al. A candidate X-linked mental retardation gene is a component of a new family of histone deacetylase-containing complexes. *J. Biol. Chem.* 278, 7234-7239 (2003).
6. Hakimi, M. A. et al. A core-BRAF35 complex containing histone deacetylase mediates repression of neuronal-specific genes. *Proc. Natl Acad. Sci. USA* 99, 7420-7425 (2002).
7. Eimer, S. et al. Loss of spr-5 bypasses the requirement for the *C. elegans* presenilin sel-12 by derepressing hop-1. *EMBO J.* 21, 5787-5796 (2002).
8. Metzger, E. et al. A novel inducible transactivation domain in the androgen receptor: implications for PRK in prostate cancer. *EMBO J.* 22, 270-280 (2003).
9. Schüle, R. et al. Functional antagonism between oncoprotein c-Jun and the glucocorticoid receptor. *Cell* 62, 1217-1226 (1990).
10. Verrijdt, G. et al. Functional interplay between two response elements with distinct binding characteristics dictates androgen specificity of the mouse sex-limited protein enhancer. *J. Biol. Chem.* 277, 35191-35201 (2002).
11. Sun, Z., Pan, J. & Balk, S. P. Androgen receptor-associated protein complex binds upstream of the androgen-responsive elements in the promoters of human prostate-specific antigen and kallikrein 2 genes. *Nucleic Acids Res.* 25, 3318-3325 (1997).
12. Brummelkamp, T. R., Bernards, R. & Agami, R. A system for stable expression of short interfering RNAs in mammalian cells. *Science* 296, 550-553 (2002).
13. Müller, J. M. et al. FHL2, a novel tissue-specific coactivator of the androgen receptor. *EMBO J* 19, 359-369 (2000).
14. Müller, J. M. et al. The transcriptional coactivator FHL2 transmits Rho signals from the cell membrane into the nucleus. *EMBO J.* 21, 736-748 (2002).
15. Shang, Y., Myers, M. & Brown, M. Formation of the androgen receptor transcription complex. *Mol. Cell.* 9, 601-610 (2002).
16. Shatkina, L. et al. The cochaperone Bag-1L enhances androgen receptor action via interaction with the NH2-terminal region of the receptor. *Mol. Cell. Biol.* 23, 7189-7197 (2003).
17. Schneider, R. et al. Direct binding of INHAT to H3 tails disrupted by modifications. *J. Biol. Chem.* 279, 23859-23862 (2004).
18. Wiznerowicz, M. & Trono, D. Conditional suppression of cellular genes: lentivirus vector-mediated drug-inducible RNA interference. *J. Virol.* 77, 8957-8961 (2003).

What is claimed is:

1. A method of treating prostate cancer in a mammal, wherein said method comprises administering to a mammal suffering from prostate cancer an effective dose of a pharmaceutical composition that comprises at least one amine oxidase inhibitor capable of blocking a demethylating activity of lysine-specific demethylase (LSD1) to inhibit androgen receptor-dependent gene expression in the mammal.

2. The method of claim 1, wherein a demethylating action of LSD1 on repressing histone marks on histone H3 is blocked.

3. The method of claim 2, wherein the histone marks on histone H3 comprise histone marks on lysine residue 9(H3-K9).

4. The method of claim 3, wherein the histone marks on histone H3 comprise histone marks on at least one of mono- and dimethyl H3-K9.

5. The method of claim 1, wherein the mammal is a human.

* * * * *